United States Patent [19]
Rozga et al.

[11] Patent Number: 5,688,237
[45] Date of Patent: Nov. 18, 1997

[54] IMPLANTABLE CATHETER AND METHOD OF USE

[75] Inventors: Jacek Rozga, Westlake Village; Achilles A. Demetriou, Bel Air, both of Calif.

[73] Assignee: Cedars-Sinai Medical Center, Los Angeles, Calif.

[21] Appl. No.: 434,460

[22] Filed: May 4, 1995

[51] Int. Cl.$^6$ ............................................. A61M 31/00
[52] U.S. Cl. ................................. 604/53; 604/93; 604/96
[58] Field of Search ........................... 604/93, 96, 101, 604/102, 185, 173, 175, 183, 186, 53; 606/191, 194

[56] References Cited

U.S. PATENT DOCUMENTS

| | | |
|---|---|---|
| 4,588,394 | 5/1986 | Schulte et al. . |
| 4,673,394 | 6/1987 | Fenton, Jr. et al. . |
| 4,692,146 | 9/1987 | Hilger . |
| 4,911,717 | 3/1990 | Gaskill, III . |
| 5,009,234 | 4/1991 | Alt . |
| 5,084,015 | 1/1992 | Moriuchi . |
| 5,085,644 | 2/1992 | Watson et al. . |
| 5,143,062 | 9/1992 | Peckham . |
| 5,300,048 | 4/1994 | Drewes, Jr. et al. . |
| 5,314,471 | 5/1994 | Brauker et al. . |
| 5,336,178 | 8/1994 | Kaplan et al. . |
| 5,339,808 | 8/1994 | Don Michel . |
| 5,425,714 | 6/1995 | Johnson et al. . |
| 5,498,539 | 3/1996 | Harrison et al. . |
| 5,516,336 | 5/1996 | McInnes et al. . |

FOREIGN PATENT DOCUMENTS 2737855  3/1979  Germany .

*Primary Examiner*—Corrine M. McDermott
*Assistant Examiner*—Deborah B. Blyveis
*Attorney, Agent, or Firm*—Pretty, Schroeder & Poplawski

[57] ABSTRACT

An implantable catheter comprises a flexible elongated catheter body having an inflatable balloon positioned near its distal end. At least one distal delivery port is located distal of the balloon and at least one proximal delivery port is located proximal of the balloon. The balloon and the distal and proximal delivery ports are connected in fluid communication with individual lumens. The lumen connected to the balloon is connected to a balloon inflation port at the proximal end of the catheter. The lumens connected to the distal and proximal delivery ports are connected to distal and proximal injection ports. Preferably, the balloon inflation port and the distal and proximal injection ports are all built into an integrated port assembly adapted for implantation under the skin of a medical patient. In use, the distal end of the catheter is inserted and fed into a passageway such as a blood vessel until the balloon and delivery ports lie within a region of interest. The port assembly is then implanted under the patient's skin. Once in place, the balloon can be inflated to occlude the flow of fluid through the passageway, and therapeutic agents can be delivered either distal or proximal of the balloon by injection into the appropriate injection port. It is believed that the catheter is particularly suited to the delivery of hepatocytes and an anticoagulant during a course of cell therapy directed to a patient's liver.

9 Claims, 1 Drawing Sheet

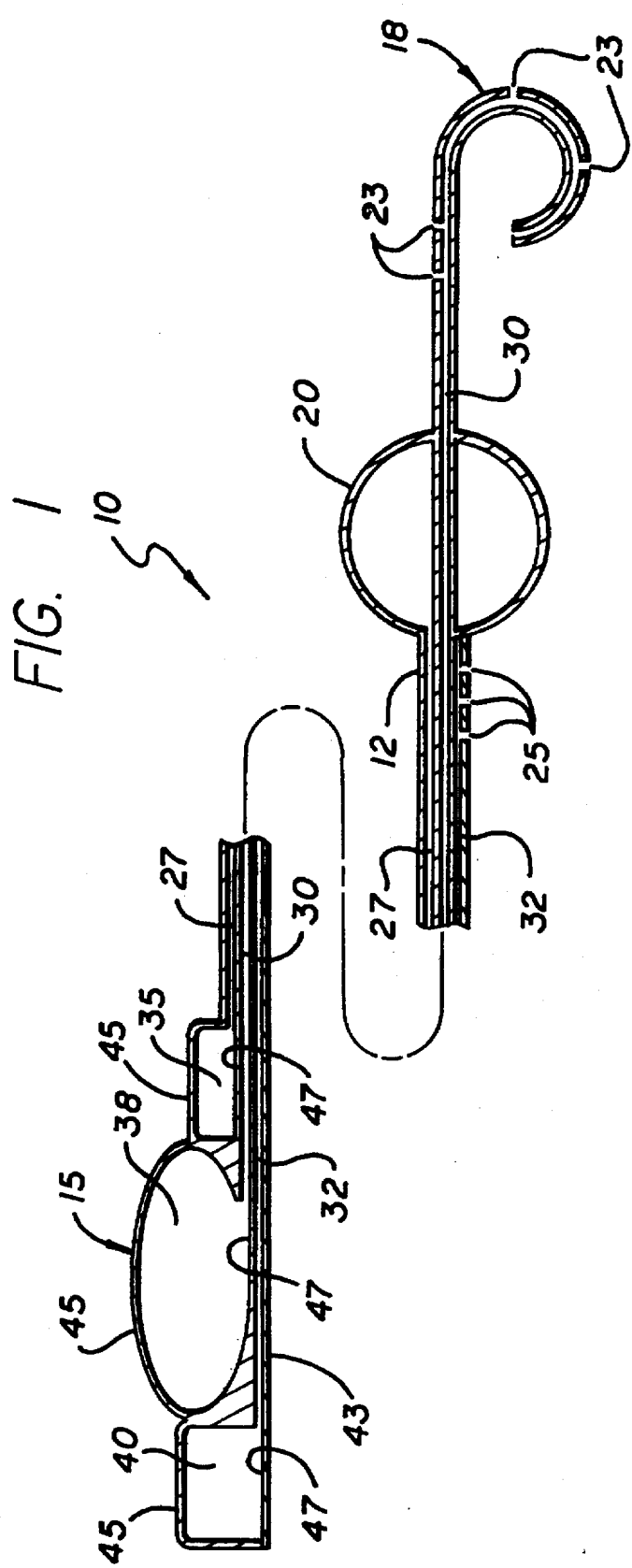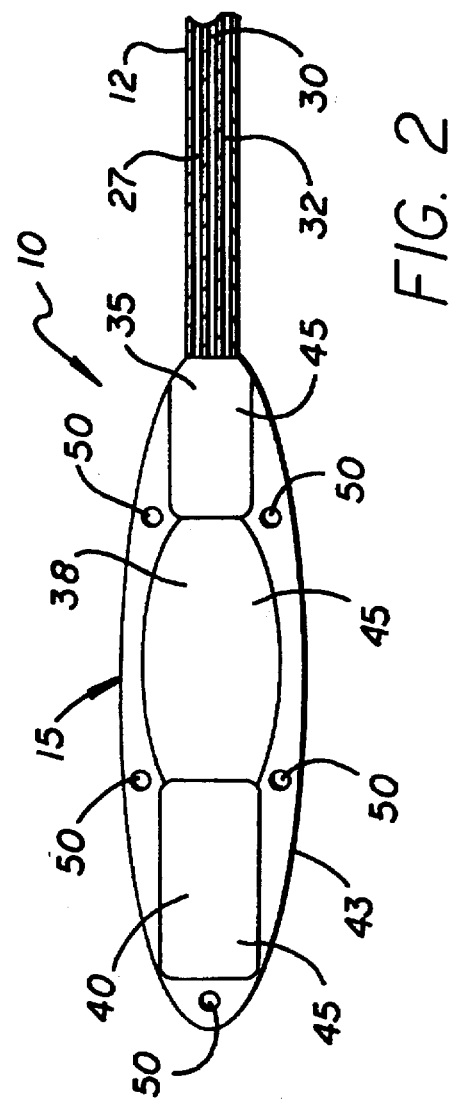

IMPLANTABLE CATHETER AND METHOD OF USE

BACKGROUND OF THE INVENTION

The invention relates generally to apparatus and methods for delivering therapeutic agents to a localized region within the body of a medical patient. More particularly, the invention relates to an implantable catheter, and a related method of using a catheter, in which drugs, cells, dispersed tissue, or other therapeutic agents are delivered through the catheter to a localized region within the body of the patient.

Therapeutic agents such as drugs are often used to combat undesirable conditions in a medical patient. Commonly, the therapeutic agent is delivered generally, e.g., orally or by intravenous injection, and dispersed more or less uniformly throughout the patient's body. In many cases, these methods of general administration can achieve a sufficient concentration of the therapeutic agent to effectively treat the undesirable condition.

In certain situations, however, adverse side effects of the therapeutic agent render effective treatment by general administration dangerous or effectively impossible. For example, the treatment of cancerous tumors by chemotherapy requires the presence of carcinostatic agents in relatively high concentrations at the site of the tumor. Unfortunately, the agents used tend to cause serious adverse side effects that may prevent or seriously interfere with the achievement of the required concentrations by general administration. For these reasons, efforts have been made to provide apparatus and methods for the local administration of therapeutic agents directly to the site of the tumor inside the patient's body.

More recently, efforts have been made to develop improved procedures for delivering cells from a donor to a localized region within the body of a patient. For example, methods are being developed in which hepatocytes, or liver cells, are delivered into a specific region of the patient's liver. There are certain dangers involved with these methods however, and one of these dangers is that blood clotting may lead to the formation of thrombotic lesions within the liver. To counteract this, it is anticipated that it may prove desirable to conduct a second therapeutic agent, an anticoagulant for example, into the same region as the hepatocytes. It should be appreciated, therefore, that a definite need exists for an implantable catheter, and a related method of using a catheter, in which therapeutic agents, such as cells, dispersed tissue, or drugs, are effectively delivered to a localized region within the body and in which a combination of suitable therapeutic agents, such as hepatocytes and anticoagulants, can be effectively delivered as well.

SUMMARY OF THE INVENTION

The present invention, which addresses this need, resides in an apparatus and related method for delivering therapeutic agents to a region of interest inside the body of a medical patient. The invention provides a catheter including a flexible elongated catheter body having a balloon located between its proximal and distal ends. One or more distal delivery ports are located distal of the balloon and one or more proximal delivery ports are located proximal of the balloon.

The balloon is connected to and in fluid communication with a balloon inflation lumen that runs the length of the catheter body member. The balloon inflation lumen is in turn connected to and in fluid communication with a balloon inflation port at the proximal end of the catheter. The distal and proximal delivery ports are connected, respectively, to first and second delivery lumens running the length of the catheter. The first and second delivery lumens are connected to distal and proximal injection ports at the proximal end of the catheter. In more detailed aspects of the invention, the balloon inflation port and the distal and proximal injection ports are all built into an integrated port assembly that is configured for implantation under the skin of a medical patient.

In use, the distal end of the catheter is fed through an incision into a blood vessel or other passageway leading to a region of interest within the patient's body. Typically, all or selected parts of the catheter will be made of radiopaque materials for convenient fluoroscopic imaging during placement of the catheter. When the balloon and the distal and proximal delivery ports are in place in the region of interest, the port assembly may be implanted under the skin of the patient.

The balloon can be inflated to impede the flow blood and other fluids through the passageway by injecting a suitable inflation fluid into the balloon inflation port and through the balloon inflation lumen. Therapeutic agents can be delivered to the region of interest either distal or proximal to the balloon by injecting the therapeutic agents into the distal or proximal injection ports. From the distal and proximal injection ports, the therapeutic agents flow through the first and second delivery lumens and the distal and proximal delivery ports into the region of interest.

Different therapeutic agents may be delivered distal and proximal of the balloon and the flow of the therapeutic agents away from their regions of delivery may be limited by inflating the balloon to block the flow of fluid through the passageway.

In another aspect of the invention, the catheter of the invention is used to deliver cells and an anticoagulant to the region of interest to perform cell therapy. To this end, the therapeutic agents advantageously, but not necessarily, include hepatocytes and a suitable anticoagulant. The hepatocytes are delivered to an injured or diseased liver through the distal delivery ports while an anticoagulant is delivered through the proximal delivery ports. Alternatively, the hepatocytes are delivered through the proximal delivery ports while an anticoagulant is delivered through the distal ports. During delivery of these agents, the anticoagulant is prevented by the inflated balloon from entering the region wherein the hepatocytes are delivered. It is believed that the apparatus and method of the invention will allow for more convenient and effective cell therapy of the liver than would previously have been possible.

Other features and advantages of the invention will become apparent from the following detailed description of the preferred embodiment, taken in conjunction with the accompanying drawings, which illustrate by way of example the principles of the invention.

BRIEF DESCRIPTION OF THE DRAWINGS

FIG. 1 is a diagrammatic cross-sectional view of an implantable catheter according to the invention; and FIG. 2 is a plan view of an integrated port assembly for use with the implantable catheter of FIG. 1.

DESCRIPTION OF THE PREFERRED EMBODIMENTS

FIG. 1 provides a diagrammatic cross-sectional view of an implantable catheter 10 according to the invention. As depicted therein, the implantable catheter comprises a flexible elongated catheter body 12 having a proximal end 15 and a distal end 18. A portion of the catheter body between the balloon and the distal end of the catheter may be in a curved, highly flexible, "pigtail" configuration, as shown. Typically, all or selected parts of the catheter will be composed of radiopaque materials for convenient and effective fluoroscopic imaging during and after placement inside the patient.

An inflatable balloon 20 is located on the catheter body 12 close to, but at some distance proximal of, the distal end 18 of the catheter 10. One or more distal delivery ports 23 are located distal to the balloon. One or more proximal delivery ports 25 are located proximal to the balloon. The delivery ports are appropriately sized openings or slits in the wall of the catheter body.

The balloon 20, the distal delivery ports 23, and the proximal delivery ports 25 are each in fluid communication with an individual lumen in the catheter body 12. The balloon is connected to a balloon inflation lumen 27, the distal delivery ports to a first delivery lumen 30, and the proximal delivery ports to a second delivery lumen 32.

Each of the lumens is connected to and in fluid communication with a port near the proximal end 15 of the catheter 10. The balloon inflation lumen 27 is connected to a balloon inflation port 35, the distal delivery port to a distal injection port 38, and the proximal delivery port to a proximal injection port 40.

The balloon inflation port 35, distal injection port 38, and proximal injection port 40 are all advantageously built into an integrated port assembly 43. (See FIGS. 1-2.) As is conventional, the upper surfaces 45 of the individual ports can be made of a flexible self-sealing material that is penetrable by a hypodermic needle connected to a syringe. Conversely, the lower backing surfaces 47 of the ports are preferably made of a rigid material to prevent accidental penetration of the needle entirely through the port assembly. As depicted in FIG. 2, the port assembly will usually be provided with one or more apertures 50 for anchoring the port assembly to tissue, such as muscle inside the patient.

In the embodiment shown, distal injection port 38 is intended for the injection of hepatocytes. With this in mind, the interior of the distal injection port has a rounded configuration without sharp corners. This configuration helps to prevent the deposition of hepatocytes as "sludge" in the corners of the injection port. Because there are no sharp restrictive corners, the hepatocytes tend not to collect in the injection port. Any hepatocytes that are deposited in the injection port can be conveniently flushed out by the injection of a suitable fluid, e.g., saline, into the injection port and out of the distal delivery port 23 at the distal end 18 of the catheter 10.

The placement of the catheter 10 within the body of a patient and the manner of the catheter's delivery of one or more therapeutic agents to a localized region of the human body will now be discussed with particular emphasis on delivery to the patient's liver. In order to place the catheter 10 shown in FIG. 1, a puncture or incision is made to provide access to an appropriate passageway, usually a blood vessel, inside the patient. During this placement, the balloon 20 is uninflated. The distal end 18 of the catheter is inserted and fed into the passageway until the balloon 20, distal delivery ports 23, and proximal delivery ports 25 are positioned as desired in close proximity to the region of interest.

With the distal end 18 of the catheter 10 in place, a further incision is then made so that the port assembly 43 can be anchored to suitable tissue inside the patient and implanted under a layer of skin. The incisions are then sutured and the wounds allowed to heal with the catheter, including the port assembly, implanted and anchored inside the patient.

For the purpose of delivering a therapeutic agent through the catheter 10 to the region of interest, a care giver need only insert a hypodermic needle through the patient's skin and into either the distal or proximal injection ports 38 or 40 to inject the agent into the injection port. From the injection port 38 or 40, the agent flows through the corresponding lumen to either the distal or proximal delivery port 23 or 25, and from there into the region of interest inside the patient's body.

If desired, the balloon 20 can be inflated by injecting an appropriate inflation solution into the balloon inflation port 35. When it is no longer desired to have the balloon inflated, fluid can be withdrawn, e.g., by a syringe, from the inflation port to deflate the balloon.

It is anticipated that the implantable catheter 10 of the invention may find particular application in connection with the delivery of hepatocytes to a diseased or injured liver during a regimen of cell therapy. In this application, the catheter is inserted and implanted inside a blood vessel with the distal and proximal delivery ports 23 and 25 and the balloon 20 in close proximity to the region to be treated.

With the catheter 10 in place, the balloon 20 is inflated to impede or block the flow of blood through the vessel. While the balloon is inflated, a first therapeutic agent, which may consist of hepatocytes, is injected into the region of interest through either the distal or the proximal injection port 38 or 40, and from there through the distal or proximal delivery port 23 or 25 near the distal end 18 of the catheter. It is contemplated that in the embodiment shown hepatocytes will normally be injected into the distal injection port for delivery to the region of interest through the distal delivery port.

In order to inhibit the formation of thrombotic lesions that might otherwise form as a result of reduced blood flow through the vessel, a second therapeutic agent may be injected into the patient on either the same or the opposite side of the balloon 20 as the first therapeutic agent. For this purpose, the second therapeutic agent may be an anticoagulant, such as heparin sodium. In light of the advantageous employment of ports situated on both sides of the balloon, the second therapeutic agent is preferably but not necessarily injected on the opposite side of the balloon as the first therapeutic agent so that the second therapeutic agent does not interfere with the action of the first. It will be appreciated that the therapeutic agents may be delivered either upstream or downstream of the balloon with respect to the direction of blood flow through the vessel.

The present invention thus provides a novel implantable catheter, and a related method of using a catheter, in which multiple therapeutic agents can be effectively delivered to a desired region of the human body. Although the invention has been described with reference to presently preferred embodiments, it should be understood that various modifications can be made without departing from the spirit or scope of the invention. The invention is defined only by the following claims.

What is claimed is:

1. A method of using an implantable catheter to treat a localized region within the body of a patient, the catheter including a flexible elongated catheter body and an inflatable balloon located on the catheter body between the proximal and distal ends of the catheter body, the catheter body having a balloon inflation lumen and first and second delivery lumens, and an implantable integrated port assembly having a balloon inflation port, a distal injection port, and a proximal injection port, each of these ports having an upper surface made of flexible, self-sealing material configured for penetration by the syringe after implantation of the catheter into the body, the method comprising:

(a) inserting the balloon and the catheter body from its distal end into a region of interest in the body;

(b) inserting the port assembly under the skin of the body;

(c) inflating the balloon by injecting fluid into the balloon inflation port;

(d) conducting hepatocytes into the region of interest through the distal delivery port; and (e) conducting an anticoagulant into the region of interest through the proximal delivery port.

2. A method according to claim 1, wherein the conducting of the anticoagulant occurs after the conducting of the hepatocytes.

3. An implantable catheter for delivering therapeutic agents to a localized region within a body, the agents delivered to the catheter by a syringe extending through the skin of the body, the catheter comprising:

a flexible elongated catheter body;

an inflatable balloon located on the catheter body; and wherein the catheter body has a proximal end and a distal end, the proximal end including an implantable integrated port assembly having a balloon inflation port, a distal injection port, and a proximal injection port, each of these ports having an upper surface made of flexible, self-sealing material for penetration by the syringe after implantation of the catheter into the body; and the distal end including (a) a balloon inflation lumen in fluid communication with the balloon and the balloon inflation port, (b) a first delivery lumen defining a distal delivery port situated distal to the balloon and through which a first therapeutic agent is delivered from the distal injection port, and (c) a second delivery lumen defining a proximal delivery port situated proximal to the balloon and through which a second therapeutic agent is delivered from the proximal injection port.

4. A catheter according to claim 3, wherein one injection port defines a rounded interior surface substantially devoid of sharp corners.

5. A catheter according to claim 1, wherein the injection port that defines a rounded interior surface substantially devoid of sharp corners is the distal injection port.

6. A catheter according to claim 3, wherein:

the first delivery lumen defines a plurality of distal delivery ports situated distal to the balloon; and the second delivery lumen defines a plurality of proximal delivery ports situated proximal to the balloon.

7. A catheter according to claim 3, wherein a part of the catheter body is made of a radiopaque material.

8. A catheter according to claim 3, wherein the ports on the proximal end each include lower backing surfaces made of a rigid material adapted to prevent accidental penetration of the syringe needle through the port assembly.

9. A catheter according to claim 3, wherein the port assembly defines one or more apertures that anchor the port assembly to tissue inside the body.

* * * * *